United States Patent [19]

Hydes et al.

[11] 4,228,090
[45] Oct. 14, 1980

[54] COMPOSITIONS CONTAINING PLATINUM

[75] Inventors: Paul C. Hydes; David M. Watkins, both of Reading, England

[73] Assignee: Johnson, Matthey & Co., Limited, London, England

[21] Appl. No.: 31,875

[22] Filed: Apr. 18, 1979

[30] Foreign Application Priority Data

Apr. 20, 1978 [GB] United Kingdom ............... 15658/78
May 26, 1978 [GB] United Kingdom ............... 22966/78

[51] Int. Cl.² .............................................. C07F 15/00
[52] U.S. Cl. ................................................. 260/429 R
[58] Field of Search .................................... 260/429 R

[56] References Cited

U.S. PATENT DOCUMENTS

| 4,119,653 | 10/1978 | Tobe et al. | 260/429 R |
| 4,119,654 | 10/1978 | Tobe et al. | 260/429 R |
| 4,140,707 | 2/1979 | Cleare et al. | 260/429 R |

OTHER PUBLICATIONS

Chemical Abstracts 77 159606p (1972).
Chemical Abstracts 80 32040f (1974).
Chemical Abstracts 80 995/v (1974).
Chemical Abstracts 83 125410d (1975).
Belluco et al. Organometallic & Coordination Chemistry of Plat. Academic Press N.Y. pp. 25, 28, 29, 30, 67, 87, 553, 556, 561, 569, 570 (1974).
Connors et al., Chem. Biol. Interactions 5, pp. 418-420 (1972).
Leh et al., J. of Pharmaceutical Sciences 65 (3), pp. 315, 318, 319, 322 (1976).
Chemical Abstracts 78 51935b (1973).
Chemical Abstracts 84 83508e (1976).
Chemical Abstracts 79 26673c (1973).
Koord Chim 2, pp. 1396-1402, 1534-1537 (1976).

Primary Examiner—Helen M. S. Sneed
Attorney, Agent, or Firm—Cushman, Darby & Cushman

[57] ABSTRACT

A coordination compounds of platinum having the Structure:

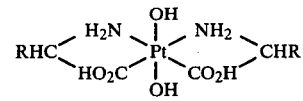

in which R is H or Me and pharmaceutical compositions containing them are disclosed.

1 Claim, No Drawings

COMPOSITIONS CONTAINING PLATINUM

This invention relates to platinum co-ordination compounds and to pharmaceutical compositions containing them.

According to a first aspect of the present invention, a composition of matter comprises a co-ordination compound of platinum having the formula:

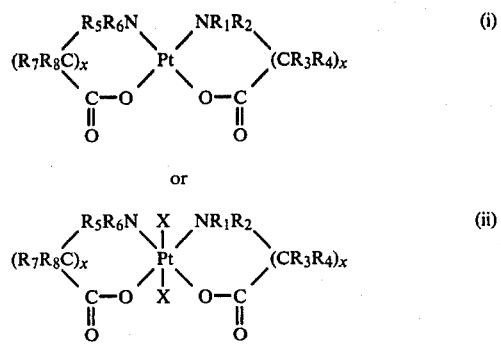

in which x is 1, 2 or 3 and the R groups are the same or different and are selected from hydrogen, substituted or unsubstituted straight-or branched-chain alkyl, aryl, alkaryl, aralkyl alkenyl, cycloalkyl, and cycloalkenyl, halogen, pseudohalogen (as hereinafter defined) hydroxy, formyl, amido, amino, alkoxy, aryloxy, sulphonic acid or salt and carboxylic acid ester or salt or two R groups may together represent oxygen or sulphur, and the X groups in formula (ii) present are halogen, psuedohalgoen or hydroxy groups.

Where one or more of the R groups is carboxylate or a derivative thereof such as ester, the general formula of which is $C_nR^1_{2n+1}CO_2^-$, it may be a substituted carboxylate such that n is an integer from 1 to 9 inclusive and the $R^1$ groups are the same or different and are selected from hydrogen, substituted or unsubstituted straight-or branched-chain alkyl, aryl, alkaryl, aralkyl, alkenyl, cycloalkyl and cycloalkenyl, halogen, pseudohalogen (as hereinafter defined), hydroxy, alkoxy, aryloxy, formyl, nitro, amido, amino, and sulphonic acid salts. We intend the above definition also to include oxygen and sulphur, such that one doubly-bonded oxygen or sulphur atom is represented by two $R^1$ groups.

Examples of particular amino acids which may be used to form a complex with platinum according to the invention are glycine ($NH_2CH_2CO_2H$), alanine ($CH_3CH(NH_2)CO_2H$), valine ($(CH_3)_2(CHCH(NH_2)CO_2H)$, phenylalanine ($PhCH_2CH(NH_2)CO_2H$), aspartic acid ($HO_2CCH_2CH(NH_2)CO_2H$), asparagine ($NH_2COCH_2CH(NH_2)CO_2H$) and cysteine ($HSCH_2CH(NH_2)CO_2H$), leucine (($CH_3)_2CHCH_2CH(NH_2)CO_2H$) and glutamic acid ($HO_2C(CH_2)_2CH(NH_2)CO_2H$). 3 aminobutyric acid and 4 aminobutyric acid are examples of $\beta$ and $\alpha$ amino acids respectively which may also be used to form a complex of platinum according to the invention.

The term "pseudohalogen" in this specification has the meaning given on p. 560 of "Advanced Inorganic Chemistry" by Cotton and Wilkinson, Interscience Publishers, 1966 as being "a molecule consisting of more than two electronegative atoms which, in the free state, resembles the halogens; these pseudohalogens give rise to anions which resemble the halide ions in behaviour". Examples of suitable pseudohalogens are cyanide, cyanate, thiocyanate and azide.

Normally the compound is used in association with a pharmaceutically acceptable carrier therefor. Accordingly, in a second aspect, the present invention provides a pharmaceutical composition which comprises a compound according to the first aspect of the invention and a pharmaceutically-acceptable carrier for said compound; these composition can be formulated so as to be suitable, for example, for parenteral or oral administration to animals.

Preparative details of complexes of platinum according to the invention will now be described by way of example.

cis-bis (glycinato)platinum (II)

(1) Preparation of cis- $Pt(NH_2CH_2COO)_2$ $K_2[PtCl_4]$ (50 g) in 200 ml hot water was charcoaled and filtered hot through a pre-heated sinter into glycine (53.52 g) and KOH (40 g) (6 mole equivalents) in 100 ml warm water. The solution was transferred to a beaker and heated on a hot plate for 20 minutes to decolourisation of the solution. The solution was then cooled to room temperature and stirred vigorously whilst concentrated HCl (30 ml) was slowly added. The precipitated white complex was filtered off on a pore three sinter, washed copiously with water and dried in vacuo at 50° C.

The white solid was suspended in 250 ml water at 80° C. for three hours, the cooled solution filtered through a pore three sinter and the product washed with water and dried in vacuo at 60° C.

Yield = 29.90 g (73%)

| Assay: | Pt | C | H | N | O |
|---|---|---|---|---|---|
| Calculated % for [Pt(NH$_2$CH$_2$COO)$_2$] | 58.85 | 13.99 | 2.36 | 8.16 | 18.65 |
| Found % | — | 13.99 | 1.83 | 6.21 | — |

(2) cis-bis(alaninato)Platinum (II)

Preparation of cis[Pt(an)$_2$](2)

where an =

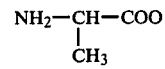

A solution of $K_2[PtCl_4]$ (50 g) in hot water (250 ml) was added to alanine (42.34 g) and potassiun hydroxide (26.68 g) in hot water (75 m) and the resulting solution heated on a hot plate until it had become pale yellow (approximately one hour). Concentrated HCl (9.9 ml) was then added dropwise to bring the solution pH to approximately three and the solution heated on a hot plate for four hours to a volume of 325 ml. The white preciptate from the cooled solution was filtered off on a pore three sinter, washed with water, ethanol and ether and dried in vacuo at 60° C.

Yield = 8.8 g (20%)

Further crops of cis[Pt(an)$_2$] were obtained by evaporating the mother liquor to 225 ml, followed by cooling to room temperature. The total yield was 13 g (30%).

| Assay: | Pt | C | H | N | O |
|---|---|---|---|---|---|
| Calculated % for cis-Pt(NH$_2$CH(CH$_3$)COO)$_2$ | 52.56 | 19.40 | 3.26 | 7.54 | 17.24 |
| Found % | — | 19.25 | 3.27 | 7.59 | — |

(3) Cis-bis (glycinato)-trans-dihydroxoplatinum (IV)
Preparation of [Pt(OH)$_2$(gly)$_2$]

where gly=NH$_2$CH$_2$COO$^-$cis-[Pt(gly)$_2$] (1.78 g) suspended in 100 vol. H$_2$O$_2$ (20 ml) was heated on a hot plate at 45° C. for ten minutes. The mixture was cooled to room temperature and the creamy precipitate filtered off on a pore three sinter, washed with water (10 ml), ethanol and ether and air dried at room temperature.

Yield=1.45 g (74%)

| Assay: | Pt | C | H | N | O |
|---|---|---|---|---|---|
| Calculate % for [Pt(OH)$_2$(NH$_2$CH$_2$COO)$_2$] | 51.73 | 12.73 | 2.67 | 7.42 | 25.45 |

| Assay: | Pt | C | H | N | O |
|---|---|---|---|---|---|
| Found % | — | 12.69 | 2.73 | 7.50 | — |

(4) cis-bis(alaninato)-trans-dihydroxoplatinum (IV)
Preparation of [Pt(OH)$_2$(an)$_2$]

cis-[Pt(an)$_2$] (3.75 g), was suspended in 100 vol. H$_2$O$_2$ (30 ml) at 45° C. for ten minutes. The mixture was cooled to room temperature, the white product filtered off on a pore three sinter, washed with water, ethanol and ether and dried in vacuo at 60° C.

Yield=3.25 g (79%)

| Assay: | Pt | C | H | N | O |
|---|---|---|---|---|---|
| Calculated % for [Pt(OH)$_2$(NH$_2$CH(CH$_3$)COO)$_2$] | 48.15 | 17.77 | 3.48 | 6.91 | 23.69 |
| Found % | — | 17.00 | 3.53 | 6.55 | — |
| [Pt(OH)$_2$(NH$_2$CH(CH$_3$)COO)$_2$]H$_2$O requires | | 17.01 | 3.81 | 6.61 | |

We claim:
1. A coordination compound of platinum having the structure:

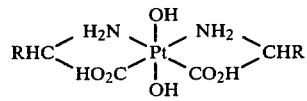

in which R is H or Me.